United States Patent
Gioia et al.

(10) Patent No.: US 9,936,691 B2
(45) Date of Patent: Apr. 10, 2018

(54) EMULSIFIABLE CONCENTRATE COMPRISING A DINITROANILINE COMPOUND

(75) Inventors: Paul Gioia, Victoria (AU); Wagner Celio Ferraz Lourenco, Campinas (BR)

(73) Assignee: RHODIA OPERATIONS, Aubervilliers (FR)

( * ) Notice: Subject to any disclaimer, the term of this patent is extended or adjusted under 35 U.S.C. 154(b) by 195 days.

(21) Appl. No.: 14/125,195

(22) PCT Filed: Jun. 27, 2012

(86) PCT No.: PCT/EP2012/062483
§ 371 (c)(1),
(2), (4) Date: Dec. 30, 2013

(87) PCT Pub. No.: WO2013/004569
PCT Pub. Date: Jan. 10, 2013

(65) Prior Publication Data
US 2014/0113825 A1   Apr. 24, 2014

Related U.S. Application Data

(60) Provisional application No. 61/504,031, filed on Jul. 1, 2011, provisional application No. 61/532,424, filed on Sep. 8, 2011.

(51) Int. Cl.
*A01N 25/02* (2006.01)
*A01N 25/04* (2006.01)
*A01N 33/18* (2006.01)

(52) U.S. Cl.
CPC ............ *A01N 25/02* (2013.01); *A01N 25/04* (2013.01); *A01N 33/18* (2013.01)

(58) Field of Classification Search
CPC ........ A01N 33/18; A01N 41/06; A01N 43/40; A01N 25/02; A01N 25/04
USPC ......................................................... 504/347
See application file for complete search history.

(56) References Cited

FOREIGN PATENT DOCUMENTS

| AU | 2007306326 B2 | 4/2008 |
|---|---|---|
| DE | 298 473 A5 | 2/1992 |
| WO | 2007030887 A1 | 3/2007 |
| WO | 2008034602 A2 | 3/2008 |
| WO | 2008043807 A1 | 4/2008 |
| WO | WO 2008043807 A1 * | 4/2008 |

OTHER PUBLICATIONS

M.V. Rathnam et al., "Density and Viscosity of Binary Mixtures of n-Butyl Acetate with Ketones at (298.15, 303.15, 308.15, and 313.15) K", Journal of Chemical and Engineering Data, May 18, 2012, pp. 1721-1727, XP055038178, DOI: 10.1021/je300085z.

* cited by examiner

*Primary Examiner* — Johann R Richter
*Assistant Examiner* — Courtney A Brown
(74) *Attorney, Agent, or Firm* — Jarrod N. Raphael

(57) ABSTRACT

The present invention relates to an emulsifiable concentrate comprising an active ingredient being a dinitroaniline compound, preferably selected from the group consisting of pendimethalin, trifluralin, benfluralin, butralin, dinitramine, ethalfluralin, fluazinam, fluchloralin, flumetralin, oryzalin, prodiamine and mixtures thereof. The emulsifiable concentrate of the invention avoids especially crystallization at low temperature when the concentration of the active ingredient is high.

17 Claims, No Drawings

EMULSIFIABLE CONCENTRATE COMPRISING A DINITROANILINE COMPOUND

This application is a U.S. national phase entry under 35 U.S.C. § 371 of International Application No. PCT/EP2012/062483, filed on Jun. 27, 2012, which claims priority to U.S. Provisional Application Nos. 61/504,031 filed on Jul. 1, 2011 and 61/532,424 filed on Sep. 8, 2011, the entirety of both of which is being incorporated herein by reference for all purposes.

BACKGROUND OF THE INVENTION

The present invention relates to an emulsifiable concentrate comprising an active ingredient being a dinitroaniline compound, preferably selected from the group consisting of pendimethalin, trifluralin, benfluralin, butralin, dinitramine, ethalfluralin, fluazinam, fluchloralin, flumetralin, oryzalin, prodiamine and mixtures thereof.

The emulsifiable concentrate of the invention prevents, and even avoids, especially crystallization at low temperature when the concentration of the active ingredient is high.

Emulsifiable concentrates (EC) are liquid compositions comprising an active ingredient in a liquid form, for example an active ingredient having a biological effect on plants (agricultural active). Emulsifiable concentrates usually have a single phase. Emulsifiable concentrates are to be mixed with water, in order to obtain a direct emulsion having a liquid hydrophobic phase comprising the active ingredient dispersed in water. For example a farmer would mix an emulsifiable concentrate comprising a hydrophobic agricultural active with water and readily obtain an emulsion to be applied onto a field. This procedure, where the farmer prepares from a concentrated composition the final product to be applied onto a field, is usually referred to as a "tank mix" procedure. An emulsifiable concentrate is also referred to as a "tank mix" composition.

Emulsifiable concentrates comprising an active ingredient being a dinitroaniline compound are known. However it is difficult to formulate these active agents at relatively high concentrations, especially at concentrations higher than 480 g/L, with sufficient stability. In particular, from a certain concentration, the formulation start to crystallize, in particular at low temperature, especially in a cold test (0° C. by 7 days) and/or during dilution and/or during storage of the dilute composition at high temperature. The crystals may have harmful effects, especially blocking the filters of the devices used for spreading the dilute composition, blocking the spraying devices, reducing the overall activity (especially bioefficacy) of the formulation, creating unnecessary problems of waste-management procedures for removing the crystals, and/or causing poor distribution of the active product on the agricultural field.

There is thus a need for new solvent systems and/or emulsifier systems and/or emulsifiable concentrates that address at least one of the following:

ability to dissolve large amounts of dinitroaniline compounds, especially at concentrations of at least 435 g/l, especially of at least 480 g/l, for example of at least 520 g/L, for example of at least 550 g/L, for example of at least 600 g/L or even of more than 600 g/L, ability to prevent, and even to avoid, crystallization problems of dinitroaniline compounds, especially when present in large amounts in emulsifiable concentrates, especially at concentrations of at least 435 g/l, for example of at least 480 g/l, for example of at least 520 g/L, for example of at least 550 g/L, for example of at least 600 g/L or even of more than 600 g/L, even under rigorous conditions such as at 0° C. by 24 hours, for example by 48 hours, for example by 72 hours, even by 7 days, and even under more rigorous conditions, such as at −5° C. by 24 hours, for example by 48 hours, for example by 72 hours, even by 7 days, ability to promote crystal redissolution, especially dinitroaniline compounds crystal redissolution, for example in high concentrated dinitroaniline compounds formulations, such as formulations comprising at least 435 g/l, especially at least 480 g/l, for example at least 520 g/L, for example at least 550 g/L, for example at least 600 g/L or even more than 600 g/L of dinitroaniline compounds, while keeping an acceptable efficacy or equivalent efficacy or even improving efficacy.

BRIEF SUMMARY OF THE INVENTION

The invention addresses at least one of the concerns above, or a combination thereof.

Thus the invention relates to a solvent composition (S1) comprising a mixture of solvents, comprising at least:
i) from 20 to 40% by weight, for example from 25 to 35% by weight, of an alkyl acetate whose alkyl group contains at least 3 carbon atoms,
ii) from 0 to 25% by weight, for example from 5 to 25% by weight, for example from 10 to 20% by weight, of 2-ethylhexyl acetate, and
iii) from 45 to 65% by weight, for example from 50 to 60% by weight, of an aromatic ketone,
these amounts being expressed relative to the sum of the solvents i), ii) and iii), equal to 100%.

The invention also relates to a solvent composition (S2) comprising a mixture of solvents, comprising at least:
i') from 30 to 50% by weight, for example from 35 to 45% by weight, of an alkyl acetate whose alkyl group contains at least 3 carbon atoms,
ii') from 35 to 55% by weight, for example from 40 to 50% by weight, of a diester solvent, and
iii') from 5 to 25% by weight, for example from 10 to 20% by weight of aromatic hydrocarbons,
these amounts being expressed relative to the sum of the solvents I'), ii') and iii'), equal to 100%.

The solvent compositions of the invention make it possible to prepare stable emulsifiable concentrates comprising dinitroaniline compounds, especially at high levels.

Thus the invention also relates to an emulsifiable concentrate comprising at least:
a) an active ingredient being a dinitroaniline compound, preferably selected from the group consisting of pendimethalin, trifluralin, benfluralin, butralin, dinitramine, ethalfluralin, fluazinam, fluchloralin, flumetralin, oryzalin, prodiamine and mixtures thereof,
b) an emulsifier or an emulsifier mixture, and
c) a solvent mixture, with said solvent mixture being selected from the solvent compositions (S1) and (S2) defined above.

The invention also relates to a method for preparing an emulsion of an active ingredient being a dinitroaniline compound, preferably selected from the group consisting of pendimethalin, trifluralin, benfluralin, butralin, dinitramine, ethalfluralin, fluazinam, fluchloralin, flumetralin, oryzalin, prodiamine and mixtures thereof, in water, comprising the step of mixing 1 part by volume of the emulsifiable concentrate of the invention, with at least 10 parts by volume of water, and up to 1000 parts by volume of water. For example the volume ratio between the emulsifiable concentrate and water may range from 0.1 to 20% v/v, preferably from 1 to 5% v/v.

The invention also relates to an emulsion comprising:
a) an active ingredient being a dinitroaniline compound, preferably selected from the group consisting of pendimethalin, trifluralin, benfluralin, butralin, dinitramine, ethalfluralin, fluazinam, fluchloralin, flumetralin, oryzalin, prodiamine and mixtures thereof,
b) an emulsifier or a mixture of emulsifiers,
c) a solvent mixture, with said solvent mixture being selected from the solvent compositions (S1) and (S2) defined above, and
water.

The emulsifiable concentrates, the emulsions formed therefrom, and the emulsions according to the invention have a good biological activity (selective herbicidal activity for destroying most annual grasses and many annual broadlevel weeds) and/or a low toxicity.

The solvent compositions and/or emulsifier systems and/or emulsifiable concentrates and/or emulsions according to the invention are stable, even at low temperature.

The solvent compositions and/or emulsifier systems and/or emulsifiable concentrates and/or emulsions according to the invention prevent, or even avoid, crystallization problems at low temperature and/or at high level of actives, in the solvent composition or emulsifiable concentrate itself or when mixing with water.

For example it can prevent, or even avoid, crystallization problems at 0° C., or even at −5° C., by 24 hours, for example 48 hours, for example 72 hours, or even by 7 days, and concentrations of up to 435 g/l, especially of up to 480 g/l, for example of up to 520 g/L, for example of up to 550 g/L, for example of up to 600 g/L prior to mixing with water. Unexpectedly, and as illustrated in the Examples, it can also promote redissolution of the crystal formed in the solvent composition or emulsifiable concentrate itself or when mixing with water.

In a preferred embodiment, the solvent compositions and/or emulsifier systems and/or emulsifiable concentrates and/or emulsions according to the invention do not give rise to crystalline precipitates for at least 48 hours upon storage at 0° C., and preferably do not give rise to crystalline precipitates for at least 72 hours and most preferably at least 7 days.

The ability to store the composition of the invention for a sustained period of time is beneficial, as it allows the user to purchase a concentrated composition and store the composition until it is desired for use without fear of loss of efficacy over time. As a result wastage of the composition and costs associated with the disposal of unused dinitroaniline compound is minimized. Furthermore, as the dinitroaniline-based composition of the invention forms stable compositions, any risk associated with the clogging of equipment or incorrect dosage of the dinitroaniline compound may be avoided.

The ability of the composition to remain stable at cold ambient temperature is advantageous for use in countries that experience cold climates, such as in many parts of Europe, Asia and North America. As the compositions of the invention resist the formation of crystallization particles even at cold storage, the useful lifetime of the composition is greatly increased in such countries.

According to one embodiment, the solvent compositions and/or emulsifier systems and/or emulsifiable concentrates and/or emulsions according to the invention are non-flammable.

The solvent compositions and/or emulsifier systems and/or emulsifiable concentrates and/or emulsions according to the invention may especially have a flash point greater than 60° C.

Advantageously solvent compositions and/or emulsifier systems and/or emulsifiable concentrates and/or emulsions according to the invention having a flash point greater than 60° C. make it possible to address at least some of the issues discussed previously (i.e. ability to dissolve large amounts of dinitroaniline compounds and/or ability to prevent, and even to avoid, crystallization problems of dinitroaniline compounds, even under rigorous conditions and/or ability to promote crystal redissolution while keeping an acceptable efficacy or equivalent efficacy or even improving efficacy) while at the same time reducing the amount of inconveniences in terms of safety, transport, storage and manipulation by the manufacturer and end user.

DETAILED DESCRIPTION OF THE INVENTION

Definitions

In the present patent application, the term "concentrate" means a formulation intended to be mixed with water (for example diluted) by the user, as opposed to a dilute composition.

In the present patent application, when concentration ranges or percentage proportions in a composition or a formulation are used, the total with optionally other ingredients is 100%. Unless otherwise mentioned, this is a concentration or proportion by weight of active material or of solids.

In the present patent application, when concentration ranges or proportions in g/L in a composition or a formulation are used, the total, with optionally other ingredients, is such that it is in accordance with the density of the composition or of the formulation (per 1 L, the total is equal to the density×1000).

Active Ingredient

According to the present invention, the active ingredient is a dinitroaniline compound.

Dinitroanilines (more specifically 2,6-dinitroanilines) are a group of herbicides used to control many grasses and broadleaf weeds. The dinitroanilines are most commonly used as pre-emergent herbicides and are incorporated in soil to control weeds in many important crops such as soybean, cotton, tobacco, tomatoes, cereals, canola, pulses and legume crops.

According to one embodiment, the dinitroaniline compound of the invention may be selected from the group consisting of pendimethalin (or N-(ethylpropyl)-3,4-dimethyl-2,6-dinitrobenzenamine), trifluralin (or α,α,α-trifluoro-2,6-dinitro-N,N-dipropyl-p-toluidine), benfluralin, butralin, dinitramine, ethalfluralin, fluazinam, fluchloralin, flumetralin, oryzalin, prodiamine and mixtures thereof.

Preferably, the dinitroaniline compound is selected from the group consisting of pendimethalin, trifluralin, ethalfluralin and mixtures thereof.

For example, the dinitroaniline compound of the invention may be composed of at least 50% by weight of trifluralin and optionally of one or both of pendimethalin and ethalfluralin.

According to one preferred embodiment, the dinitroaniline compound of the invention is trifluralin.

According to another preferred embodiment, the dinitroaniline compound of the invention is pendimethalin.

Solvent Mixtures

As indicated previously, the invention relates to solvent mixtures that make it possible to prepare stable emulsifiable concentrates comprising dinitroaniline compounds, especially at high levels.

Solvent Composition (S1)

According to a first embodiment, the invention relates to a solvent composition (S1) comprising at least:
an alkyl acetate whose alkyl group contains at least 3 carbon atoms,
  optionally, but preferably, 2-ethylhexyl acetate, and
  an aromatic ketone.

The invention relates more specifically to a solvent composition (S1) comprising a mixture of solvents, comprising at least:
i) from 20 to 40% by weight, for example from 25 to 35% by weight, of an alkyl acetate whose alkyl group contains at least 3 carbon atoms,
ii) from 0 to 25% by weight, for example from 5 to 25% by weight, for example from 10 to 20% by weight, of 2-ethylhexyl acetate, and
iii) from 45 to 65% by weight, for example from 50 to 60% by weight, of an aromatic ketone,
these amounts being expressed relative to the sum of the solvents i), ii) and iii), equal to 100%.

In a preferred embodiment, the solvent composition (S1) comprises 2-ethylhexyl acetate, in an amount ranging from 5 to 25% by weight relative to the total weight of the solvent composition. The additional presence of 2-ethylhexyl acetate makes it possible to improve the overall performances of the resulting emulsifiable concentrate and resulting emulsion.

It may especially be a solvent composition consisting of:
i) an alkyl acetate whose alkyl group contains at least 3 carbon atoms, in an amount ranging from 20 to 40% by weight, for example from 25 to 35% by weight,
ii) 2-ethylhexyl acetate, in an amount ranging from 5 to 25% by weight, for example from 10 to 20% by weight, and
iii) an aromatic ketone, in an amount ranging from 45 to 65% by weight, for example from 50 to 60% by weight,
these amounts being expressed relative to the sum of the solvents i), ii) and iii), equal to 100%.

Alkyl Acetate Whose Alkyl Group Contains at Least 3 Carbon Atoms

According to the invention, the alkyl acetate whose alkyl group contains at least 3 carbon atoms is different from 2-ethylhexyl acetate.

Advantageously, the alkyl group of the "alkyl acetate whose alkyl group contains at least 3 carbon atoms" is a $C_6$-$C_{15}$, preferably $C_6$-$C_{13}$ and preferably $C_6$-$C_{12}$ alkyl. It may especially be a linear, branched or cyclic $C_6$, $C_7$, $C_8$, $C_9$, $C_{10}$, $C_{11}$, $C_{12}$ or $C_{13}$ alkyl. It may be a mixture of such alkyls. Mention may preferably be made especially of cyclohexyl or hexyl (n-hexyl), octyl (n-octyl), isooctyl, decyl (n-decyl), isodecyl, tridecyl, dodecyl and undecyl.

Preferably the alkyl acetate whose alkyl group contains at least 3 carbon atoms of the invention is cyclohexyl acetate.

Aromatic Ketone

Suitable aromatic ketones comprise, in addition to an aromatic group, an aliphatic radical which is substituted by a ketone group. Suitable aromatic ketones are, for example, acetophenone or alkoxy-substituted acetophenone derivatives such as 4-methoxyacetophenone.

Preferably the aromatic ketone of the invention is acetophenone.

According to a preferred embodiment, the solvent composition (S1) of the invention comprises at least:
i) from 20 to 40% by weight, for example from 25 to 35% by weight, of cyclohexyl acetate,
ii) from 5 to 25% by weight, for example from 10 to 20% by weight, of 2-ethylhexyl acetate,
iii) from 45 to 65% by weight, for example from 50 to 60% by weight, of acetophenone, these amounts being expressed relative to the sum of the solvents i), ii) and iii), equal to 100%.

It may especially be a solvent composition consisting of:
i) cyclohexyl acetate, in an amount ranging from 20 to 40% by weight, for example from 25 to 35% by weight,
ii) 2-ethylhexyl acetate, in an amount ranging from 5 to 25% by weight, for example from 10 to 20% by weight, and
iii) acetophenone, in an amount ranging from 45 to 65% by weight, for example from 50 to 60% by weight,
these amounts being expressed relative to the sum of the solvents i), ii) and iii), equal to 100%.

Solvent Composition (S2)

According to a second embodiment, the invention relates to a solvent composition (S2) comprising at least:
an alkyl acetate whose alkyl group contains at least 3 carbon atoms,
a diester solvent, and
aromatic hydrocarbons.

The invention relates more specifically to a solvent composition (S2) comprising a mixture of solvents, comprising at least:
i') from 30 to 50% by weight, for example from 35 to 45% by weight, of an alkyl acetate whose alkyl group contains at least 3 carbon atoms,
ii') from 35 to 55% by weight, for example from 40 to 50% by weight, of a diester solvent,
iii') from 5 to 25% by weight, for example from 10 to 20% by weight of aromatic hydrocarbons,
these amounts being expressed relative to the sum of the solvents i'), ii') and iii'), equal to 100%.

It may especially be a solvent composition consisting of:
i') an alkyl acetate whose alkyl group contains at least 3 carbon atoms, in an amount ranging from 30 to 50% by weight, for example from 35 to 45% by weight,
ii') a diester solvent, in an amount ranging from 35 to 55% by weight, for example from 40 to 50% by weight,
iii') aromatic hydrocarbons, in an amount ranging from 5 to 25% by weight, for example from 10 to 20% by weight,
these amounts being expressed relative to the sum of the solvents i'), ii') and iii'), equal to 100%.

Alkyl Acetate Whose Alkyl Group Contains at Least 3 Carbon Atoms

According to the invention, the alkyl acetate whose alkyl group contains at least 3 carbon atoms is different from 2-ethylhexyl acetate.

Advantageously, the alkyl group of the "alkyl acetate whose alkyl group contains at least 3 carbon atoms" is a $C_6$-$C_{15}$, preferably $C_6$-$C_{13}$ and preferably $C_6$-$C_{12}$ alkyl. It may especially be a linear, branched or cyclic $C_6$, $C_7$, $C_8$, $C_9$, $C_{10}$, $C_{11}$, $C_{12}$ or $C_{13}$ alkyl. It may be a mixture of such alkyls. Mention may preferably be made especially of cyclohexyl or hexyl (n-hexyl), octyl (n-octyl), isooctyl, decyl (n-decyl), isodecyl, tridecyl, dodecyl and undecyl.

Preferably the alkyl acetate whose alkyl group contains at least 3 carbon atoms of the invention is cyclohexyl acetate.

Diester Solvent

The diester solvent suitable in the solvent composition (S2) of the invention may especially be provided in the form of a mixture comprising the dicarboxylic acid diesters of the following formulae (I'), (I") and optionally (II):

optionally $R^1$—COO—$(CH_2)_4$—COO—$R^2$ (II) (adipic acid diester),
where:
$A_{MG}$ is a group of formula —$CH(CH_3)$—$CH_2$—$CH_2$—,
$A_{ES}$ is a group of formula —$CH(C_2H_5)$—$CH_2$—.

In these formulae (I'), (I") and (II), the $R^1$ and $R^2$ groups can in particular be methyl, ethyl or isobutyl groups. $R^1$ and $R^2$ are preferably methyl groups.

According to a particularly preferred embodiment of the present invention, the mixture of diesters comprises:

from 70 to 95% by weight of the dicarboxylic acid diester of formula (I'), preferably of the dimethyl ester, from 5 to 30% by weight of the dicarboxylic acid diester of formula (I"), preferably of the dimethyl ester, and from 0 to 10% by weight of the dicarboxylic acid diester of formula (II), preferably the dimethyl ester.

As an example of such a mixture of diesters, mention may be made especially of the mixture marked by Rhodia under the name Rhodiasolv® IRIS, which is a mixture of diesters comprising essentially (more than 80 wt %) of dimethyl ethylsuccinate and dimethyl 2-methylglutarate. The diester solvent described above is considered as green solvent having a low Volatile Organic Compound behavior and/or a low toxicity.

Aromatic Hydrocarbons

The aromatic hydrocarbons suitable in the solvent composition (S2) of the invention may especially be selected from aromatic hydrocarbon solvents such as toluene, xylenes, polynuclear aromatic hydrocarbons such as naphthalenes and alkylnaphthalenes and mixtures thereof, many of which are available from the fractionation of crude oil and in general have distillation ranges in the temperature range of about 135° C. to 305° C., with those having a distillation range of from about 183° C. to 290° C. being most preferred.

The aromatic hydrocarbons of the invention may especially be a mixture of $C_8$-$C_{12}$ di- and trialkyl benzenes having a flash point of at least 60.5° C.

Such mixtures are commercially available under a variety of tradenames, e.g. SOLVESSO 200 and AROMATIC 200 both commercially available from Exxon, Fareham, Hants, United Kingdom.

According to a preferred embodiment, the solvent composition (S2) of the invention comprises at least:
i') from 30 to 50% by weight, for example from 35 to 45% by weight, of cyclohexyl acetate,
ii') from 35 to 55% by weight, for example from 40 to 50% by weight, of a diester solvent comprising from 70 to 95% by weight of the dimethyl ester of 2-methylglutaric acid, from 5 to 30% by weight of the dimethyl ester of 2-ethylsuccinic acid, and from 0 to 10% by weight of the dimethyl ester of adipic acid, and
iii') from 5 to 25% by weight, for example from 10 to 20% by weight of a mixture of $C_8$-$C_{12}$ di- and trialkyl benzenes having a flash point of at least 60.5° C., these amounts being expressed relative to the sum of the solvents i'), ii') and iii'), equal to 100%.

It may especially be a solvent composition consisting of:
i') cyclohexyl acetate, in an amount ranging from 30 to 50% by weight, for example from 35 to 45% by weight,
ii') a diester solvent comprising from 70 to 95% by weight of the dimethyl ester of 2-methylglutaric acid, from 5 to 30% by weight of the dimethyl ester of 2-ethylsuccinic acid, and from 0 to 10% by weight of the dimethyl ester of adipic acid, in an amount ranging from 35 to 55% by weight, for example from 40 to 50% by weight, and
iii') a mixture of $C_8$-$C_{12}$ di- and trialkyl benzenes having a flash point of at least 60.5° C., in an amount ranging from 5 to 25% by weight, for example from 10 to 20% by weight, these amounts being expressed relative to the sum of the solvents i'), ii') and iii'), equal to 100%.

The present invention relates to the solvent compositions (S1) and (S2) as such.

The present invention also relates to any compositions comprising or consisting of (a) a solvent composition selected from (S1) and (S2) and (b) an active ingredient being a dinitroaniline compound, preferably selected from the group consisting of pendimethalin, trifluralin, benfluralin, butralin, dinitramine, ethalfluralin, fluazinam, fluchloralin, flumetralin, oryzalin, prodiamine and mixtures thereof.

It may especially be an emulsifiable concentrate as described below.

Emulsifiable Concentrate

The present invention further relates to an emulsifiable concentrate comprising at least:
a) an active ingredient being a dinitroaniline compound, preferably selected from the group consisting of pendimethalin, trifluralin, benfluralin, butralin, dinitramine, ethalfluralin, fluazinam, fluchloralin, flumetralin, oryzalin, prodiamine and mixtures thereof,
b) an emulsifier or an emulsifier mixture, and
c) a solvent mixture, with said solvent mixture being selected from the solvent compositions (S1) and (S2) defined above.

Active Ingredient

The emulsifiable concentrate of the invention may comprise at least 435 g/l, especially at least 480 g/l, for example at least 520 g/L, for example at least 550 g/L, for example at least 600 g/L or even more than 600 g/L of the dinitroaniline compound of the invention.

For example the emulsifiable concentrate of the invention may comprise at least 30% by weight, for example at least 40% by weight, for example from about 45% to about 65% by weight, for example from about 48% to about 55% by weight of the dinitroaniline compound of the invention, relative to the total weight of the emulsifiable concentrate.

The emulsifiable concentrate of the invention may contain one or more dinitroaniline compounds. When it contains more than one dinitroaniline compound, the total dinitroaniline compound content is preferably in the ranges as defined above.

The emulsifiable concentrate of the invention may comprise, in addition to dinitroaniline compounds, one or more additional herbicides, for example herbicides having a complementary action.

Emulsifier or Emulsifier Mixture

The emulsifiable concentrate of the invention comprises also an emulsifier or a mixture of emulsifiers.

The emulsifier or emulsifier mixture assists in compatibilizing the herbicidal components of the composition and stabilizing the composition of the present invention through the formation of emulsion or dispersions.

The emulsifiable concentrate of the invention preferably includes two or more emulsifiers.

The emulsifier mixture is to be adapted depending on the solvent mixture, extension of dilution required for use of the concentrate and the period of physical stability required following dilution prior to use.

According to the invention, the emulsifier or mixture of emulsifiers is preferably selected from the group consisting of the following compounds:

anionic surfactants such as alkylbezenesufonates such as dodecylbenzenesulfonates, for example calcium dodecylbenzensulfonate, ethoxylated and/or propoxylated di- or tri-styrylphenol phosphates, ethoxylated and/or propoxylated di- or tri-styrylphenol sulfates, phenyl sulfonates, alkynaphtalenesulphonates, ethoxylated and/or propoxylated alcohol phosphate esters, ethoxylated and/or propoxylated alkylaryl phosphate esters, taurates, suphosuccinates, polycarboxylates, nonionic surfactants such as ethoxylated and/or propoxylated di- or tri-styrylphenols, ethoxylated and/or propoxylated fatty alcohols, ethoxylated and/or propoxylated fatty amines, ethoxylated and/or propoxylated alkylphenols such as ethoxylated nonylphenols, block copolymers having polypropylene glycol blocks and polyethylene glycol blocks, sorbitan esters, ethoxylated oleic acids, ethoxylates castor oils, and mixtures thereof.

More especially it has been found that the following emulsifier mixture (E) is well adapted when the solvent mixture is selected from the solvent compositions (S1) and (S2) of the invention.

According to one embodiment, the emulsifier mixture of the invention is an emulsifier mixture (E) comprising:

at least 30 g/l (relative to the emulsifiable concentrate), for example from 35 g/l to 60 g/l, of an alkaline metal or alkaline metal salts of dodecylbenzene sulfonic acid, such as calcium dodecylbenzene sulfonate (CaDDBS), for example RHODACAL® 60/BE-C marketed by Rhodia, a 60% CaDDBS solution in ethylhexanol, or RHODACAL® 70 marketed by Rhodia, a 60% CaDDBS solution in isobutanol, and preferably of a 60% CaDDBS solution in ethylhexanol, at least 35 g/l (relative to the emulsifiable concentrate), preferably from 40 g/l to 50 g/l, of ethoxylated and/or propoxylated di- or tri-styrylphenols, preferably of ethoxylated and propoxylated tristyrylphenols, for example SOPROPHOR® TSP/724 marketed by Rhodia, and optionally at least 20 g/l (relative to the emulsifiable concentrate), preferably from 20 g/l to 30 g/l, of ethoxylated and/or propoxylated alkylphenols, preferably of ethoxylated and propoxylated nonylphenols, for example ANTAROX® 461 P marketed by Rhodia.

The emulsifier or mixture of emulsifiers, and the amounts thereof, are such that an emulsifiable concentrate is obtained.

When the solvent mixture is the solvent composition (S1), the emulsifier mixture is preferably an emulsifier mixture (E1) comprising, and preferably consisting of:

at least 45 g/l (relative to the emulsifiable concentrate), for example from 50 g/l to 60 g/l, for example about 55 g/l, of an alkaline metal or alkaline metal salts of dodecylbenzene sulfonic acid, such as calcium dodecylbenzene sulfonate (CaDDBS), for example RHODACAL® 60/BE-C marketed by Rhodia, a 60% CaDDBS solution in ethylhexanol, or RHODACAL® 70 marketed by Rhodia, a 60% CaDDBS solution in isobutanol, and preferably of a 60% CaDDBS solution in ethylhexanol, and at least 35 g/l (relative to the emulsifiable concentrate), preferably from 40 g/l to 50 g/l, for example 45 g/l, of ethoxylated and/or propoxylated di- or tri-styrylphenols, preferably of ethoxylated and propoxylated tristyrylphenols, for example SOPROPHOR® TSP/724 marketed by Rhodia.

When the solvent mixture is the solvent composition (S2), the emulsifier mixture is preferably an emulsifier mixture (E2) comprising, and preferably consisting of:

at least 30 g/l (relative to the emulsifiable concentrate), for example from 32 g/l to 40 g/l, for example about 35 g/l, of an alkaline metal or alkaline metal salts of dodecylbenzene sulfonic acid, such as calcium dodecylbenzene sulfonate (CaDDBS), for example RHODACAL® 60/BE-C marketed by Rhodia, a 60% CaDDBS solution in ethylhexanol, or RHODACAL® 70 marketed by Rhodia, a 60% CaDDBS solution in isobutanol, and preferably of a 60% CaDDBS solution in ethylhexanol, at least 35 g/l (relative to the emulsifiable concentrate), preferably from 35 g/l to 45 g/l, for example about 40 g/l, of ethoxylated and/or propoxylated di- or tri-styrylphenols, preferably of ethoxylated and propoxylated tristyrylphenols, for example SOPROPHOR® TSP/724 marketed by Rhodia, and at least 20 g/l (relative to the emulsifiable concentrate), preferably from 20 g/l to 30 g/l, for example about 25 g/l, of ethoxylated and/or propoxylated alkylphenols, preferably of ethoxylated and propoxylated nonylphenols, for example ANTAROX® 461 P marketed by Rhodia.

It has been found that the emulsifier mixtures (E), (E1) and (E2) of the invention are particularly advantageous in that they make it possible to achieve good emulsion properties while maintaining the solvent mixtures effects, especially on crystallization.

The present invention relates to the emulsifier mixtures (E), (E1) and (E2) as such.

The present invention also relates to any compositions comprising or consisting of:
(a) a solvent composition selected from (S1) and (S2),
(b) any emulsifier mixture (E),
and optionally (c) an active ingredient being a dinitroaniline compound, preferably selected from the group consisting of pendimethalin, trifluralin, benfluralin, butralin, dinitramine, ethalfluralin, fluazinam, fluchloralin, flumetralin, oryzalin, prodiamine and mixtures thereof.

The present invention also relates to a composition comprising or consisting of:
(a) the solvent composition (S1),
(b) the emulsifier mixture (E1),
and optionally (c) an active ingredient being a dinitroaniline compound, preferably selected from the group consisting of pendimethalin, trifluralin, benfluralin, butralin, dinitramine, ethalfluralin, fluazinam, fluchloralin, flumetralin, oryzalin, prodiamine and mixtures thereof.

The present invention also relates to a composition comprising or consisting of:
(a) the solvent composition (S2),
(b) the emulsifier mixture (E2),
and optionally (c) an active ingredient being a dinitroaniline compound, preferably selected from the group consisting of pendimethalin, trifluralin, benfluralin, butralin, dinitramine, ethalfluralin, fluazinam, fluchloralin, flumetralin, oryzalin, prodiamine and mixtures thereof.

Solvent Mixture

The emulsifiable concentrate of the invention comprises also a solvent mixture, which may be selected from the solvent compositions (51) and (S2) of the invention.

The emulsifiable concentrate of the invention may comprise at least 20% by weight, for example from 30 to 60% by weight, for example from 35 to 55% by weight, of the solvent mixture of the invention, relative to the total weight of the emulsifiable concentrate.

Other Compounds

The emulsifiable concentrate according to the invention might consist only of the active ingredient (a), the emulsifier or emulsifier mixture (b), and the solvent mixture (c) of the invention.

It may also comprise further ingredients, as follows.

The emulsifiable concentrate might comprise antifoaming agents. Antifoaming agents suitable for use in the compositions of the present invention include conventional antifoaming agents, with silicone based antifoaming agents such as those sold under the Silicolapse and tradenames commercially available from Rhodia, being preferred. In a preferred embodiment of the invention, an antifoaming agent is used at a level sufficient to prevent undesirable foaming during the preparation of tank mixes using the emulsion concentrates of the present invention. Typically, less than 1% by weight of a defoamer is sufficient, with amounts of about 0.01 to about 0.1% by weight being preferred.

According to one embodiment, the emulsifiable concentrate of the invention does not comprise any antifoaming agent.

The emulsifiable concentrate might comprise antigelation agents such as N-methylpyrrolidone, cyclohexanone, alcohols such as ethanol and methanol, glycols such as propylene glycol and ethylene glycol.

According to one embodiment, the emulsifiable concentrate of the invention does not comprise any antigelation agent.

The emulsifiable concentrate of the invention might comprise further active ingredients such as other herbicides and pesticides. It is preferred that these further actives be soluble in the emulsifiable concentrate, thereby forming an emulsifiable concentrate combo.

According to one embodiment, the emulsifiable concentrate of the invention does not comprise any additional active ingredient.

Preparation Process

Standard processes for preparing emulsifiable concentrates or solvent mixtures may be used. The process may be performed by simple mixing of the constituents.

Regarding the preparation of the solvent mixture of the invention, it is especially possible to introduce the various solvents separately. A solvent mixture prepared beforehand, typically the solvent composition, may also be introduced.

The solvent composition may be prepared by simple mixing of the solvents.

Regarding the emulsifiable concentrate of the invention, it may be prepared by admixing all of the ingredients in the solvent mixture. In a preferred embodiment of the present invention, the emulsifiable concentrate of the invention are prepared by a method comprising the following steps:

(a) admixing the active ingredient, for example trifluralin in a molten form into the solvent mixture, (b) adding the emulsifier(s), (c) optionally allowing cooling, and (d) filtering before packaging the emulsifiable concentrate.

In one preferred embodiment, the emulsifiable concentrate of the invention may be prepared by a method comprising the steps of:

(a) admixing the active ingredient, for example trifluralin in a molten form into the solvent mixture, (b) adding the emulsifier(s), (c) allowing cooling, and to stand for at least 1 hour, for example at least 2 hours, for example at least 4 hours, and (d) filtering before packaging the emulsifiable concentrate.

The emulsifiable concentrate compositions of the present invention are diluted with water and applied as dilute, aqueous emulsions to the locus where weed control is desired. Typical dilution rates are in the range of about 1 part by volume of concentrate per at least 10 parts, preferably at least 15 parts, up to 500 parts, for example 19 or 20 parts. While the compositions of this invention are effective for controlling weeds when employed alone, they may also be used in conjunction with or in combination with other biological chemicals, including other herbicides.

Performance

The emulsifiable concentrate according the invention is preferably such that the active ingredient, for example trifluralin, does not crystallize at 0° C. by 24 hours, for example by 48 hours, for example by 72 hours, even by 7 days, and preferably at −5° C. by 24 hours, for example by 48 hours, for example by 72 hours, even by 7 days, at a concentration of active ingredient of at least 480 g/l, especially of at least 500 g/l, for example of at least 520 g/L, for example of at least 550 g/L, for example of at least 600 g/L or even of more than 600 g/L, and/or such that it does not crystallize at these temperatures upon dilution.

Crystallization tests can be performed on the emulsifiable concentrate by seeding and observing (eye observation).

Crystallization upon dilution tests can be performed on the emulsifiable concentrate by observing (eye observation or web 45 μm sieve residue).

Use of the Compositions of the Invention

The emulsifiable concentrates, the emulsions formed therefrom, and the emulsions according to the invention are plant-protection formulations.

The emulsifiable concentrate of the invention is intended to be spread on a cultivated field or a field to be cultivated, for example a field of soybean, usually after diluting in water, to obtain a dilute composition. The dilution is generally performed by the farmer, directly in a tank (tank mix), for example in the tank of a device for spreading the composition. It is not excluded for the farmer to add other plant-protection products, for example fungicides, herbicides, pesticides, insecticides or fertilizers. Thus, the formulation may be used to prepare a composition diluted in water of the active plant-protection product, by mixing at least one part by weight of concentrated formulation with at least 10 parts and preferably less than 1000 parts of water. The dilution rates and the amounts to be applied on the field generally depend on the plant-protection product and on the desirable dose for treating the field; this may be determined by the farmer.

Other details or advantages of the invention will emerge in the light of the examples that follow, which are given without any limiting nature.

EXAMPLES

Concrete but non-limiting examples of the invention are presented below.

The following ingredients are used:
cyclohexyl acetate,
2-ethylhexyl acetate,
acetophenone,
SOLVESSO® 200, from Exxon
RHODIASOLV® IRIS, from Rhodia Trifluralin tech 96%, from Nufarm SOPROPHOR® TSP/724 from Rhodia (ethoxylated and propoxylated tristyrylphenols), RHODACAL® 60/BE-C from Rhodia (a 60% calcium dodecylbenzene sulfonate solution in ethylhexanol)

ANTAROX® 461 P from Rhodia (ethoxylated and propoxylated nonylphenols).

Examples 1 and 2

The following solvent compositions in accordance with the invention were prepared (the contents are indicated as % by weight relative to the total weight of the solvent composition):

| | EXAMPLE | |
|---|---|---|
| SOLVENT COMPOSITION | 1<br>MIX 1 | 2<br>MIX 2 |
| Cyclohexyl acetate | 30% | 40% |
| 2-Ethylhexyl acetate | 15% | — |
| Acetophenone | 55% | — |
| SOLVESSO® 200 | — | 15% |
| RHODIASOLV® IRIS | — | 45% |

These two solvent compositions were able to solubilise up to 600 g/l of trifluralin active at 0° C. by 7 days.

Moreover the flash points of these two solvent compositions are higher than 60° C. These two solvent compositions are thus additionally non flammable formulations.

Examples 3 and 4: Trifluralin 550 g/L and 600g/L Using MIX 1

The following emulsifiable concentrates were prepared according to the protocol indicated in the description (the contents are indicated as % by weight relative to the total weight of the solvent composition):

| | EXAMPLE | |
|---|---|---|
| | 3 | 4 |
| Trifluralin | 50.5%<br>(=550 g/l ae) | 54.6%<br>(=600 g/l ae) |
| SOLVENT COMPOSITION OF EXAMPLE 1 | 40.7% | 54.6% |
| RHODACAL® 60/BE-C | 4.8% | 4.8% |
| SOPROPHOR® TSP/724 | 4.0% | 4.0% |

Examples 5 and 6: Trifluralin 550 g/L and 600 g/L Using MIX 2

The following emulsifiable concentrates were prepared according to the protocol indicated in the description (the contents are indicated as % by weight relative to the total weight of the solvent composition):

| | EXAMPLE | |
|---|---|---|
| | 5 | 6 |
| Trifluralin | 49.4%<br>(=550 g/l ae) | 53.3%<br>(=600 g/l ae) |
| SOLVENT COMPOSITION OF EXAMPLE 2 | 41.9% | 38.1% |

-continued

| | EXAMPLE | |
|---|---|---|
| | 5 | 6 |
| ANTAROX® 461 P | 2.2% | 2.2% |
| RHODACAL® 60/BE-C | 3.0% | 3.0% |
| SOPROPHOR® TSP/724 | 3.5% | 3.5% |

Example 7: Performance

Emulsion Stability of Emulsifiable Concentrates (ECs) 3-6 were Evaluated as Per Test Described in CIPAC MT 36.3

The following tests are performed:

Visual observation at different temperatures: ambient temperature (21° C.) and for 24 hours in a warm temperature bath (set at 30° C.)

The appearance of the emulsions are noted and fall out of active as sludge or sedimentation is investigated, through observation.

Re-emulsification is also investigated by re-mixing the emulsions after 24 hours standing at 30° C. and placing back in the warm bath a further hour before re-assessment.

The ECs 3-6 of the invention all showed good bloom and good fine blue emulsion quality, with sludge/sedimentation after 24 hours at 30° C., from less than 0.01 ml for 550 g/l active to less than 0.7 ml for 600 g/l active, when freshly prepared or after 14 days stored at 54° C. (accelerated storage).

They all exhibited good re-emulsification properties after 24 hours.

In comparison, Nufarm Triflur 480 g/L active EC gave good bloom with an adequate emulsion, resulting with 6 ml total sedimentation plus sludge, after 24 hours at 30° C.

In practice, quality of the emulsion reflects the bio-efficacy of the formulation. Better quality and stable emulsion will give more efficacious results.

Low Temperature Crystallisation

The following tests are performed:

Visual observation after one week storage at 0° C. (respectively at −5° C.)

The formulation is placed for seven days at 0° C. (respectively at −5° C.), and the appearance of the formulation is noted and the possible presence of crystals is investigated (test CIPAC MT39)

Visual observation at 0° C. (respectively at −5° C.) with nucleation: a crystal of the active material (obtained from the dried up composition) is introduced into the formulation that has spent 7 days at 0° C. (respectively at −5° C.) for nucleation, and the formulation is placed at 0° C. (respectively at −5° C.) for a further 7 days. The appearance of the formulation is noted and the possible presence of crystals is investigated.

The containers were 12 mL glass bottles filled to 10 mL with the composition to be tested. Crystallisation was assessed visually as a percentage in volume. The amount of crystallisation was assessed by its volume relative to the 10 mL of composition.

| Ex | Visual observation at 0° C. for 7 days (without nucleous) | Visual observation at 0° C. for 7 days (with nucleous) | Visual observation at −5° C. for 7 days (without nucleous) | Visual observation at −5° C. for 7 days (with nucleous) |
| --- | --- | --- | --- | --- |
| 3 | No crystal | No crystal | No crystal | No crystal |
| 4 | No crystal | No crystal | No crystal | <7% crystals |
| NT | No crystal | No crystal | No crystal | 25% crystals |

Key: NT = Nufarm Triflur 480 g/lL ae

The solvent compositions and emulsifiers systems of the invention make it possible to obtain highly concentrated trifluralin emulsifiable concentrates able to dissolve large amounts of trifluralin and to avoid crystallisation problems under rigorous conditions.

Further experiments were conducted on composition of Example 4, in which some crystals were formed after 7 days at −5° C.

This composition was allowed to reach ambient temperature (21° C.) without agitation. Unexpectedly, these crystals re-dissolved after 5 days at ambient temperature (21° C.), without any agitation.

This illustrates that the solvent compositions and emulsifier systems of the invention make also it possible to promote crystal redissolution in high concentrated formulations.

As a comparison, the same tests were performed on the product Nufarm Triflur 480 Selective Herbicide from Nufarm, which is a commercial Emulsifiable Concentrate containing 480 g/L of trifluralin (currently the market leader in Australia).

No crystal were observed at 0° C. or −5° C. for 7 days without nucleous, or at 0° C. for 7 days with nucleous of the dried up commercial product.

At −5° C. for 7 days with nucleous of the dried up commercial product, about 25% of crystals were observed (according to the same protocol as described above).

The same further experiments were also conducted on this comparative formulation, i.e. it was allowed to reach room temperature (21° C.) without agitation.

However crystals (about 3%) were still present after three weeks at ambient temperature (21° C.) without agitation.

The invention claimed is:

1. An emulsifiable concentrate comprising:
   a) at least 550 g/L of an active ingredient being a dinitroaniline compound,
   b) an emulsifier or a mixture of emulsifiers, and
   c) a solvent mixture, wherein said solvent mixture is a solvent composition (S1) consisting of:
      i) from 20 to 40% by weight of an alkyl acetate whose alkyl group contains at least 3 carbon atoms and is different from 2-ethylhexyl acetate,
      ii) from 5 to 25% by weight of 2-ethylhexyl acetate, and
      iii) from 45 to 65% by weight of an aromatic ketone, these amounts being expressed relative to the sum of the solvents i), ii) and iii), equal to 100%.

2. The emulsifiable concentrate according to claim 1, wherein the dinitroaniline compound is selected from the group consisting of pendimethalin, trifluralin, ethalfluralin and mixtures thereof.

3. The emulsifiable concentrate according to claim 1, comprising a mixture of emulsifiers wherein the mixture is an emulsifier mixture (E) comprising:
   at least 30 g/l (relative to the emulsifiable concentrate), of an alkaline metal or alkaline metal salts of dodecylbenzene sulfonic acid,
   at least 35 g/l (relative to the emulsifiable concentrate), of ethoxylated and/or propoxylated di- or tri-styrylphenols, and optionally
   at least 20 g/l (relative to the emulsifiable concentrate), of ethoxylated and/or propoxylated alkylphenols.

4. The emulsifiable concentrate according to claim 1, wherein the solvent mixture is the solvent composition (S1) and the mixture of emulsifiers is an emulsifier mixture (E1) comprising:
   at least 45 g/l (relative to the emulsifiable concentrate), of an alkaline metal or alkaline metal salts of dodecylbenzene sulfonic acid, and
   at least 35 g/l (relative to the emulsifiable concentrate), of ethoxylated and/or propoxylated di- or tri-styrylphenols.

5. A method for preparing an emulsion of an active ingredient being a dinitroaniline compound in water, comprising the step of mixing 1 part by volume of the emulsifiable concentrate according claim 1, with at least 10 parts by volume of water, and up to 1000 parts by volume of water.

6. An emulsion comprising the emulsifiable concentrate according to claim 1 and water.

7. A composition comprising:
   (a) a solvent composition (S1) consisting of:
      i) from 20 to 40% by weight of an alkyl acetate whose alkyl group contains at least 3 carbon atoms and is different from 2-ethylhexyl acetate,
      ii) from 5 to 25% by weight of 2-ethylhexyl acetate, and
      iii) from 45 to 65% by weight of an aromatic ketone, these amounts being expressed relative to the sum of the solvents i), ii) and iii), equal to 100%;
   (b) an emulsifier mixture (E) comprising:
      at least 30 g/l (relative to the emulsifiable concentrate), of an alkaline metal or alkaline metal salts of dodecylbenzene sulfonic acid,
      at least 35 g/l (relative to the emulsifiable concentrate), of ethoxylated and/or propoxylated di- or tri-styrylphenols, and optionally
      at least 20 g/l (relative to the emulsifiable concentrate), of ethoxylated and/or propoxylated alkylphenols,
      and optionally (c) at least 550 g/L of an active ingredient being a dinitroaniline compound.

8. The composition according to claim 7 comprising:
   (a) the solvent composition (S1),
   (b) an emulsifier mixture (E1) comprising:
      at least 45 g/l (relative to the emulsifiable concentrate), of an alkaline metal or alkaline metal salts of dodecylbenzene sulfonic acid, and
      at least 35 g/l (relative to the emulsifiable concentrate), of ethoxylated and/or propoxylated di- or tri-styrylphenols,
      and optionally (c) at least 550 g/L of an active ingredient being a dinitroaniline compound.

9. The emulsifiable concentrate according to claim 1, wherein the dinitroaniline compound is selected from the group consisting of pendimethalin, trifluralin, benfluralin, butralin, dinitramine, ethalfluralin, fluazinam, fluchloralin, flumetralin, oryzalin, prodiamine and mixtures thereof.

10. The emulsifiable concentrate according to claim 1, comprising at least 600 g/L of the dinitroaniline compound.

11. The emulsifiable concentrate according to claim 4, wherein the emulsifier mixture (E1) comprises from 50 g/l to 60 g/l of an alkaline metal or alkaline metal salts of dodecylbenzene sulfonic acid.

12. The emulsifiable concentrate according to claim 4, wherein the emulsifier mixture (E1) comprises about 55 g/l of an alkaline metal or alkaline metal salts of dodecylbenzene sulfonic acid.

13. The emulsifiable concentrate according to claim 4, wherein the emulsifier mixture (E1) comprises from 40 g/l to 50 g/l of ethoxylated and/or propoxylated di- or tri-styrylphenols.

14. The emulsifiable concentrate according to claim 4, wherein the emulsifier mixture (E1) comprises 45 g/l of ethoxylated and/or propoxylated di- or tri-styrylphenols.

15. The emulsifiable concentrate according to claim 4, wherein the ethoxylated and/or propoxylated di- or tri-styrylphenols are ethoxylated and propoxylated tristyrylphenols.

16. An emulsifiable concentrate comprising:
a) at least 550 g/L of an active dinitroaniline compound selected from the group consisting of pendimethalin, trifluralin, ethalfluralin and mixtures thereof;
b) an emulsifier or a mixture of emulsifiers; and
c) a solvent mixture, wherein said solvent mixture is a solvent composition (S1) consisting of:
i) from 20 to 40% by weight of a $C_6$-$C_{15}$ alkyl acetate which is different from 2-ethylhexyl acetate;
ii) from 5 to 25% by weight of 2-ethylhexyl acetate; and
iii) from 45 to 65% by weight of an aromatic acetophenone or alkoxy-substituted acetophenone,
these amounts being expressed relative to the sum of the solvents i), ii) and iii), equal to 100%.

17. The emulsifiable concentrate according to claim 16, comprising a mixture of emulsifiers wherein the mixture is an emulsifier mixture (E) comprising:
at least 30 g/l, relative to the emulsifiable concentrate, of an alkaline metal or alkaline metal salts of dodecylbenzene sulfonic acid;
at least 35 g/l, relative to the emulsifiable concentrate, of ethoxylated and/or propoxylated di- or tri-styrylphenols; and optionally
at least 20 g/l, relative to the emulsifiable concentrate, of ethoxylated and/or propoxylated alkylphenols.

* * * * *